United States Patent
Friedrich

(10) Patent No.: US 7,034,172 B1
(45) Date of Patent: Apr. 25, 2006

(54) FERRIC AND ACID COMPLEX

(75) Inventor: Klaus Friedrich, Detroit, MI (US)

(73) Assignee: BASF Corporation, Florham Park, NJ (US)

( * ) Notice: Subject to any disclaimer, the term of this patent is extended or adjusted under 35 U.S.C. 154(b) by 0 days.

(21) Appl. No.: 11/147,088

(22) Filed: Jun. 7, 2005

(51) Int. Cl.
*C07F 15/02* (2006.01)

(52) U.S. Cl. .................. 556/148; 556/147
(58) Field of Classification Search ......... 556/147, 556/148
See application file for complete search history.

(56) References Cited

U.S. PATENT DOCUMENTS

| | | | |
|---|---|---|---|
| 4,364,871 | A | 12/1982 | Svatek et al. |
| 4,438,040 | A | 3/1984 | Svatek et al. |
| 4,451,442 | A | 5/1984 | Jeffrey et al. |
| 4,666,528 | A | 5/1987 | Arrington et al. |
| 4,741,888 | A | 5/1988 | Fong et al. |
| 4,784,838 | A | 11/1988 | Paul et al. |
| 4,791,048 | A | 12/1988 | Hirai et al. |
| 5,030,651 | A | 7/1991 | Moll et al. |
| 5,093,094 | A | 3/1992 | Van Kleeck et al. |
| 5,110,965 | A | 5/1992 | Thunberg et al. |
| 5,177,105 | A | 1/1993 | Moll et al. |
| 5,188,927 | A | 2/1993 | Okada et al. |
| 5,282,959 | A | 2/1994 | Roling et al. |
| 5,316,898 | A | 5/1994 | Ueda et al. |
| 5,356,932 | A | 10/1994 | Moll et al. |
| 5,366,853 | A | 11/1994 | Yoshimoto |
| 5,753,423 | A | 5/1998 | Buongiome et al. |
| 5,898,078 | A | 4/1999 | St. George et al. |
| 5,900,499 | A | 5/1999 | St. George et al. |
| 5,922,920 | A | 7/1999 | Bond et al. |
| 6,022,490 | A | 2/2000 | Hermant et al. |
| 6,432,900 | B1 | 8/2002 | Appel et al. |
| 6,534,253 | B1 | 3/2003 | Kuykendall et al. |
| 6,582,893 | B1 | 6/2003 | Vincent et al. |
| 6,653,271 | B1 | 11/2003 | Hage et al. |
| 6,824,965 | B1 | 11/2004 | Wichmann et al. |
| 2002/0090581 | A1 | 7/2002 | Fyson et al. |
| 2003/0165782 | A1 | 9/2003 | Wan |

FOREIGN PATENT DOCUMENTS

| | | |
|---|---|---|
| DE | 3800270 | 7/1989 |
| DE | 3622364 | 7/1996 |
| EP | 0205748 | 12/1986 |
| EP | 617008 | 9/1994 |
| FR | 2771951 | 6/1999 |
| JP | 54155038 | 12/1979 |
| JP | 58021690 | 2/1983 |
| JP | 63284154 | 11/1988 |
| JP | 1071842 | 3/1989 |
| JP | 2048558 | 2/1990 |
| JP | 6145120 | 5/1994 |
| JP | 7005650 | 1/1995 |
| JP | 8092178 | 4/1996 |
| JP | 10168046 | 6/1998 |
| JP | 2001097935 | 4/2001 |
| JP | 2001199945 | 7/2001 |
| JP | 2001226335 | 8/2001 |
| JP | 2002156733 | 5/2002 |
| JP | 2004191795 | 7/2004 |
| RU | 371041 | 3/1995 |

OTHER PUBLICATIONS

English language Abstract for JP54155038.
English language Abstract for JP58021690 extracted from espacenet.com database dated May 30, 2005.
English language Abstract for JP63284154 extracted from espacenet.com database dated May 30, 2005.
English language Abstract for JP1071842 extracted from espacenet.com database dated May 30, 2005.
English language Abstract for JP2048558 extracted from espacenet.com database dated May 30, 2005.
English language Abstract for JP6145120 extracted from espacenet.com database dated May 30, 2005.
English language Abstract for JP7005650 extracted from espacenet.com database dated May 30, 2005.
English language Abstract for JP8092178 extracted from espacenet.com database dated May 30, 2005.
English language Abstract for JP10168046 extracted from espacenet.com database dated May 30, 2005.

(Continued)

*Primary Examiner*—Porfirio Nazario-Gonzalez
(74) *Attorney, Agent, or Firm*—Fernando A. Borrego

(57) ABSTRACT

A ferric and acid complex includes the reaction product of a chelant, iron oxide, a base, and a reaction promoter. The chelant has at least one carboxylic acid functionality. The reaction promoter has an $Fe^{3+}$ ion. A process for preparing the ferric and acid complex in a vessel includes charging solvent, the chelant, the base, the iron oxide, and the reaction promoter into the vessel. The solvent, chelant, base, iron oxide, and reaction promoter are heated to a temperature of at least 170° F. for a period of at least about 3 hours to form the ferric and acid complex. Due to the use of the reaction promoter having the $Fe^{3+}$ ion, the process for preparing the ferric and acid complex results in reduced degradation of the chelant during processing and, thus, a high quality ferric and acid complex.

25 Claims, No Drawings

OTHER PUBLICATIONS

English language Abstract for JP2001097935 extracted from espacenet.com database dated May 30, 2005.
English language Abstract for JP200199945 extracted from espacenet.com database dated May 30, 2005.
English language Abstract for JP2001226335 extracted from espacenet.com database dated May 30, 2005.
English language Abstract for JP2002156733 extracted from espacenet.com database dated May 30, 2005.
English language Abstract for JP2004191795 extracted from espacenet.com database dated May 30, 2005.
English language Abstract for EP0205748 extracted from espacenet.com database dated May 30, 2005.
English language Abstract for FR2771951 extracted from espacenet.com database dated May 30, 2005.
English language Abstract for DE3800270 extracted from espacenet.com database dated May 30, 2005.
English language Abstract for RD371041.

FERRIC AND ACID COMPLEX

FIELD OF THE INVENTION

The subject invention generally relates to a ferric and acid complex. More specifically, the subject invention relates to a ferric and acid complex formed from a chelant, an iron oxide, a base, and a reaction promoter.

BACKGROUND OF THE INVENTION

Ferric and acid complexes are known in the art and are useful as photochemical reagents for developing photographic film. Conventional ferric and acid complexes are generally prepared by reacting a ferric salt and an aminocarboxylic acid chelant in water. The aminocarboxylic acid chelant has four carboxylic acid functionalities. Some of the carboxylic acid functionalities are deprotonated with ammonium hydroxide by removing a proton. A hydroxide ion of the ammonium hydroxide and one of the carboxylic acid functionalities react to produce a water molecule. In addition, the ferric salts react with the carboxylic acid functionalities to result in production of iron ions having a positive valence and removal of a proton from more of the carboxylic acid functionalities to produce water molecules. As a result, many of the carboxylic acid functionalities of the chelant are converted into carboxylate ions having a negative valence. Coordinate bonds are formed between one of the iron ions and three of the carboxylate ions of the chelant to produce the ferric and acid complex. After reacting with the carboxylic acid functionalities, the ferric salts provide iron ions having a positive valence.

One of the problems with production of the conventional complexes is that the ferric salts are expensive compared to other sources of iron. As a result, iron oxides have been used as a source of iron ions. To make the iron ions available to react with the carboxylate ions of the aminocarboxylic acid chelant, the iron source must be dissolved in water along with the aminocarboxylic acid chelant. However, iron oxides are relatively insoluble in water and require longer mix times and higher temperatures to react, as compared to the ferric salts, which more readily mix into the water due to their higher solubility. The longer mix times and higher temperatures result in an accelerated rate of degradation of the aminocarboxylic acid chelants. Degradation of the aminocarboxylic acid chelants is undesirable and impacts formation of the ferric and acid complex. Also, by-products formed from the degradation can negatively influence the desired performance of the ferric and acid complex in, for example, the photochemical application. Ferrous salts, which provide $Fe^{2+}$ ions as opposed to $Fe^{3+}$ ions, have been used to catalyze the reaction between the iron oxide and the aminocarboxylic acid chelants.

There remains an opportunity to further improve processing parameters for the ferric and acid complexes by using reaction promoters other than or in addition to the ferrous salts to minimize degradation of the chelant during processing.

SUMMARY OF THE INVENTION AND ADVANTAGES

The subject invention provides a ferric and acid complex including the reaction product of a chelant, iron oxide, a base, and a reaction promoter. The chelant has at least one carboxylic acid functionality. The reaction promoter has an $Fe^{3+}$ ion.

The subject invention also provides a process for preparing the ferric and acid complex in a vessel. To prepare the ferric and acid complex, solvent, the chelant, the base, the iron oxide, and the reaction promoter having the $Fe^{3+}$ ion are charged into the vessel. The solvent, chelant, base, iron oxide, and reaction promoter in the vessel are heated to a temperature of at least 170° F. for a period of at least about 3 hours to form the ferric and acid complex.

Due to the use of the reaction promoter having the $Fe^{3+}$ ion, the process for preparing the ferric and acid complex results in minimized degradation of the chelant during processing even more than $Fe^{2+}$, ions. Thus, the use of the reaction promoter having the $Fe^{3+}$ ion results in a higher quality ferric and acid complex than has previous been available when iron oxide is used to prepare the ferric and acid complex.

DETAILED DESCRIPTION OF A PREFERRED EMBODIMENT

A ferric and acid complex according to the subject invention may be used as a photochemical reagent for developing film. More specifically, the ferric and acid complex may be included in a bath into which exposed film is immersed in order to develop images on the film.

The ferric and acid complex includes the reaction product of a chelant and an iron oxide. As will be described in further detail below, the reaction between the chelant and the iron oxide occurs in a solvent. Preferably, the solvent is water; however, other solvents may alternatively be used. The water may be distilled water, deionized water, filtered process water, etc. The chelant and the iron oxide are dissolved in the solvent to allow the chelant and the iron oxide to react. Although the ferric and acid complex may be stored and packaged in the solvent, it is to be appreciated that the ferric and acid complex may be separated from the solvent into a solid form, such as a powder.

The chelant has at least one carboxylic acid functionality. Preferably, the chelant is an aminopolycarboxylic acid. The aminopolycarboxylic acid may have at least two carboxylic acid functionalities. The carboxylic acid functionalities are present for reaction with the iron ions, as will be described in further detail below. Nitrogen atoms that provide the amino portion of the aminopolycarboxylic acid function to stabilize the final ferric and acid complex. However, it is to be appreciated that suitable chelants may also be used that only have the carboxylic acid functionalities, absent amino functionality.

As described above, suitable aminopolycarboxylic acids for the subject invention include those that have at least one carboxylic acid functionality. For example, in one embodiment, the aminopolycarboxylic acid may have four carboxylic acid functionalities. In another embodiment, the aminopolycarboxylic acid may have three carboxylic acid functionalities. It is to be appreciated that the aminopolycarboxylic acid may also include other functionalities, such as a hydroxyl functionality. Specific examples of suitable aminopolycarboxylic acids may be selected from the group of ethylenediaminetetraacetic acid, nitrilotriacetic acid, iminodiacetic acid, 1,2-propylenediaminetetraacetic acid, N-methyl, -ethyl, -propyl and -butyl iminodiacetic acid, 1,3-propylenediaminetetraacetic acid, N-hydroxyethylethylenediaminetriacetic acid, triethylenetetraminehexaacetic acid, diethylenetriaminepentaacetic acid, and combinations thereof. Other suitable chelants may include hydroxy carboxylic acids which are capable of chelating an iron ion.

Specific examples of such hydroxy carboxylic acids may be selected from the group of citric acid, tartaric acid, lactic acid and gluconic acid.

Preferably, the chelant is present, prior to the reaction between the chelant and the iron oxide, in an amount of from 70 to 90 parts by weight based on the total weight of the ferric and acid complex. For example, the chelant may be present prior to reaction in an amount of about 72.7 parts by weight based on the total weight of the ferric and acid complex.

During the reaction between the iron oxide and the chelant, oxygen atoms of the iron oxide and protons of the carboxylic acid functionalities react, resulting in production of iron ions complexed by the chelant. Water molecules are also produced. Many of the carboxylic acid functionalities of the chelant are converted into carboxylate ions having a negative valence. In one embodiment, coordinate bonds are formed between one of the iron ions and two carboxylate ions of the chelant, when the chelant only includes two carboxylic acid functionalities, to produce the ferric and acid complex. In another embodiment, when the chelant includes three carboxylic acid functionalities, coordinate bonds are formed between one of the iron ions and four of the carboxylate ions, the surplus negative charge of the fourth carboxylate group being left to form a salt with a base, to be described in further detail below.

Iron oxides suitable for the subject invention include iron (II, III) oxides, e.g., $Fe_3O_4$, and iron (III) oxides, e.g., $Fe_2O_3$, as well as hydrated iron oxides, such as alpha-hydrated iron oxide, e.g., alpha-FeOOH, and gamma-hydrated iron oxide, e.g., gamma-FeOOH, and any combination of the iron oxides. Specific examples of suitable iron oxides may be selected from the group of magnetite, goethite, lepidocrocite, ferrihydrite, and combinations thereof. Due to the relatively higher reactivity of magnetite as compared to, for example, goethite, magnetite, which includes a mixture of iron (III) and iron (II) ions, with a majority of iron (III) ions, is particularly suitable for purposes of the subject invention.

Preferably, the iron oxides are present, prior to the reaction between the chelant and the iron oxide, in an amount of at least 16 parts by weight based on the total weight of the ferric and acid complex. For example, the iron oxides are most preferably present in an amount of from about 17.0 to about 18.5 parts by weight based on the total weight of the ferric and acid complex.

As alluded to above, the ferric and acid complex further includes the reaction product of a base. During reaction, in addition to the reaction between the iron oxides and the carboxylic acid functionalities, some of the carboxylic acid functionalities of the chelant and the base react to remove a proton from the carboxylic acid functionality. More specifically, a hydroxide ion from the base and a proton from one of the carboxylic acid functionalities react to produce a water molecule. An ion from the base remains after the reaction between the hydroxide group and the proton from the carboxylic acid functionality. As described above, coordinate bonds are formed between one of the iron ions and three of the carboxylate ions of the chelant. One of the ions from the base reacts with the fourth carboxylate ion of the chelant to balance the charges of the complex, which has an overall neutral valence.

The base also serves functions other than participation in the reaction to form the complex. More specifically, the reaction between the iron oxide and the chelant is pH-dependent. Some of the base may be charged at different points during preparation of the ferric and acid complex in order to adjust the pH value into a desired range, as will be described in further detail below. The base may also be charged prior to and/or after charging the iron oxide to aid in dissolving the chelant and/or the iron oxide in the solvent.

Any conventional base is suitable for purposes of the subject invention. Bases that are particularly suited for purposes of the subject invention include bases that are selected from the group of ammonia, ammonium hydroxide, alkyl amines, ethanol amines, propanol amines, alkali hydroxides, earthalkali hydroxides, and combinations thereof.

Preferably, the base is used in an amount of from 4 to 14 parts by weight based on the total weight of the ferric and acid complex, depending on the actual base used. For example, in one embodiment, the base is ammonium hydroxide and is used in an amount of about 8.7 parts by weight based on the total weight of the ferric and acid complex.

The ferric and acid complex also includes the reaction product of a reaction promoter having an $Fe^{3+}$ ion. More specifically, the reaction promoter preferably includes a ferric salt. Although ferric ions from the ferric salt participate in the reaction to produce the ferric and acid complex, the ferric salt from the reaction promoter is present in such a minimal amount, as set forth below, as to provide a negligible amount of iron ions for forming the ferric and acid complex. However, the presence of the ferric salt in the solvent while the iron oxide is dissolved increases a rate of dissolution of the iron oxide into the solvent and promotes the reaction between the iron oxide and the chelant. Due to the presence of the reaction promoter and the interaction between the reaction promoter and the iron oxide in the solvent, overall cycle times for preparing the ferric and acid complex are minimized. The minimized cycle time both decreases the cost of production for the ferric and acid complex and minimizes the time during which the chelant has an opportunity to degrade as a result of exposure to elevated temperatures during preparation of the ferric and acid complex.

Suitable ferric salts for purposes of the subject invention include, but are not limited to, ferric sulfate, ferric carbonate, ferric chloride, ferric nitrate, ferric bromide, ferric citrate, ferric glycolate, hydrates of the ferric salts, and combinations thereof. Particularly suitable as the reaction promoter are ferric sulfate and hydrates of the ferric sulfate, due to the relative non-corrosive nature of sulfate ions that may remain in the ferric and acid complex after reaction. Furthermore, the ferric sulfate is relatively cheap, as compared to the other ferric salts, and may be stored while maintaining reactive properties.

Preferably, the reaction promoter is present in an amount of from 0.03 to 3.5 parts by weight based on the total weight of the ferric and acid complex. For example, in one embodiment, the reaction promoter is present in an amount of about 0.2 parts by weight based on the total weight of the ferric and acid complex.

A process for preparing the ferric and acid complex occurs in a vessel. The vessel may be a reactor, a flask, or any other type of reaction vessel that allows for proper agitation, heat transfer, and charging and discharging of the materials and sampling during preparation of the ferric and acid complex. For the process, solvent, the chelant, the base, the iron oxide, and the reaction promoter are all charged into the vessel. As described below, the chelant, the iron oxide, the base, and the reaction promoter may be charged together or separately into the vessel including the solvent in any order. In one embodiment, the chelant and the solvent are mixed in the vessel for a period of at least 10 minutes prior to charging the base, iron oxide, and reaction promoter into the vessel. More specifically, the solvent may be charged into the vessel prior to charging the chelant or, alternatively, the solvent and the chelant may be charged concurrently into the vessel. The solvent and the chelant may be charged at room temperature of about 77° F. The chelant and the solvent are mixed to at least partially dissolve the chelant in the solvent and to make the chelant available for reaction.

Some of the base may be charged into the vessel prior to charging the iron oxide and the reaction promoter. More specifically, some of the base may be charged into the vessel that contains the solvent and the chelant in order to assist in dissolving the chelant in the solvent. Preferably, the base is charged into the vessel until the pH value within the vessel is less than about 4.5.

In one embodiment, the iron oxide and the reaction promoter are charged into the vessel that contains the solvent, the chelant dissolved or suspended in the solvent, and the base; however, it is to be appreciated that the solvent, the chelant, the base, the iron oxide, and the reaction promoter may be charged into the vessel concurrently. Alternatively, the chelant, the base, the iron oxide, and the reaction promoter may be charged into the vessel containing the solvent in any order. The iron oxide and the reaction promoter may be charged separately or concurrently into the vessel, and may be charged at room temperature of about 77° F. Additional base may be charged into the vessel along with or after charging the iron oxide and the reaction promoter to obtain a pH value within the vessel of from 3.6 to 4, which assists in dissolving the iron oxide in the solvent.

Once the chelant, the iron oxide, the base, and the reaction promoter have been charged in the vessel, those components are heated in the vessel to a temperature of at least 170° F. for a period of at least about 3 hours to form the ferric and acid complex. For example, the heating preferably occurs within a temperature range of from about 180° F. to about 212° F. for a period of from 3 to 12 hours, or at a temperature of about 203° F.+/−5° F. for a period of about 4 hours.

The length of time during which the components are heated is dependent upon the progression of the reaction. The progression may be visually observed in the form of a color change of the mixture in the vessel and the presence of solids, and analytically tested for pH value, iron in solution, the amount of free chelant, and/or the amount of chelant degradation products. More specifically, the components, prior to reaction, have a gray or brownish color. As the reaction progresses, the contents turn a greenish color and the solids in the mixture visibly decrease. The pH value may be measured with a standard pH meter.

The iron in solution may be measured by atom absorption spectroscopy. Preferably, the iron in solution is measured after sparging and filtration, which are described in further detail below. The iron in solution indicates how much of the iron oxide has been consumed through the reaction, which translates to an amount of the ferric and acid complex that has been formed in the reaction, assuming an appropriate amount of chelant has been charged. An acceptable amount of iron in solution is at least 98.5 parts by weight based on the total weight of all iron charged into the vessel.

The amount of free chelant indicates how much of the chelant remains unreacted and may be measured by complexometric titration. An acceptable amount of free chelant is from about 0.1 to about 5.0 percent by weight based on the total weight of all chelant charged into the vessel.

The amount of chelant degradation products indicates the quality of the ferric and acid complex and may be measured by chromatographically determining the amounts of known degradation products such as acetic acid, formic acid, oxalic acid, or certain lower aminocarboxylic acids. An acceptable amount of chelant degradation products is about 0.3 percent by weight or less based on the total weight of all chelant charged into the vessel.

A sample of the ferric and acid complex in solvent is taken from the vessel and analyzed for pH value, an amount of iron in solution, and an amount of undissolved ferric oxide. The pH value of the ferric and acid complex in solvent is then adjusted, if necessary, by adding additional base or additional chelant. The ferric and acid complex may be sparged with air to oxidize any ferrous ions that may be present into ferric ions. The ferric and acid complex in solvent may be filtered and then transferred to storage.

Preferably, after the ferric and acid complex has been prepared, the ferric and acid complex is stored and packaged in the solvent. Alternatively, the ferric and acid complex may be substantially separated from the solvent by spray drying, drum drying, or any other suitable drying operation, in which case the ferric and acid complex may be stored and packaged as a powder.

The following examples, illustrating the ferric and acid complex of the subject invention, are intended to illustrate and not to limit the invention.

EXAMPLES

Ferric and acid complexes of the subject invention are prepared by first charging solvent into a 1 liter vessel, which is a flask, at room temperature of about 77° F. The chelant is then charged into the vessel, along with a portion of the base until the pH value within the vessel is about 4. The chelant, the solvent, and the base are mixed for a period of about 10 minutes. The iron oxide and the reaction promoter are then charged into the vessel, at room temperature of about 77° F., along with more of the base to obtain a pH value within the vessel of from 3.6 to 4. The contents of the vessel are then heated to a temperature of about 203° F.+/−5° F. for a heating time, which is specified in Table 1, until the ferric and acid complex in solvent is formed. A sample of the ferric and acid complex in solvent is taken from the vessel after the heating time and analyzed for iron in solution, pH value, and undissolved iron oxide. The amount of undissolved iron oxide is determined gravimetrically. The pH value of the ferric and acid complex in solvent may then be adjusted by adding additional base or additional chelant. The ferric and acid complex in solvent is then sparged with air from the bottom of the vessel for about 30 minutes at room temperature to oxidize any ferrous ions in the vessel into ferric ions. The ferric and acid complex in solvent is then filtered and transferred to storage.

Specific components included in or used to prepare the ferric and acid complex of the subject invention are set forth in Table 1. All amounts are in parts by weight based on the total weight of the ferric and acid complex, unless otherwise stated.

TABLE 1

| Component | Ex. A | Ex. B | Ex. C |
|---|---|---|---|
| Ferric and Acid Complex | | | |
| Chelant | 72.74 | 72.73 | 72.75 |
| Base A | 8.73 | 8.75 | 8.57 |
| Iron oxide | 18.34 | 18.35 | 18.35 |
| Reaction promoter A | 0.19 | 0.17 | 0.00 |

TABLE 1-continued

| Component | Ex. A | Ex. B | Ex. C |
|---|---|---|---|
| Reaction promoter B | 0.00 | 0.00 | 0.33 |
| Total Ferric and Acid Complex in Solvent | 100.00 | 100.00 | 100.00 |
| Total amount of chelant, base, iron oxide, and reaction promoter, parts by weight based on total amount of components in the vessel | 26.93 | 26.92 | 26.93 |
| Solvent, parts by weight based on the total amount of components in the vessel | 73.07 | 73.08 | 73.07 |
| Total | 100.00 | 100.00 | 100.00 |
| Heating time, hours within heating temperature range | 6 | 8 | 6 |
| Heating temperature range, °F. | 203 +/− 5 | 203 +/− 5 | 203 +/− 5 |
| pH value of final ferric and acid complex in the solvent | 2.98 | 3.95 | 3.66 |
| Iron in solution, pbw based on the total weight of all iron charged into the vessel | 99.7 | 99.5 | 99.4 |
| Undissolved iron oxide, pbw based on the total weight of all iron oxide charged into the vessel | 0.3 | 0.5 | 0.4 |

Comparative Example A

Comparative Example A is prepared in the same manner as described above, except different reaction promoters have been used. Specific components included in or used to prepare Comparative Example A are set forth in Table 2. All amounts are in parts by weight based on the total weight of the ferric and acid complex, unless otherwise stated.

TABLE 2

| Component | Comparative Ex. A |
|---|---|
| Ferric and Acid Complex | |
| Chelant | 72.68 |
| Base A | 8.73 |
| Iron oxide | 18.32 |
| Reaction promoter C | 0.27 |
| Total Ferric and Acid Complex in Solvent | 100.00 |
| Total amount of chelant, base, iron oxide, and reaction promoter, parts by weight based on total amount of components in the vessel | 26.90 |
| Solvent, parts by weight based on the total amount of components in the vessel | 73.10 |
| Total | 100.00 |
| Heating time, hours within heating temperature range | 6 |
| Heating temperature range, °F. | 203 +/− 5 |
| pH value of final ferric and acid complex in the solvent | 3.7 |
| Iron in solution, pbw based on the total weight of all iron charged into the vessel | 98.3 |
| Undissolved iron oxide, pbw based on the total weight of all iron oxide charged into the vessel | 1.7 |

Comparative Example B

Comparative Example B is prepared without any reaction promoter. More specifically, solvent is first charged into a 1 liter vessel, which is a flask, at room temperature of about 77° F. The chelant is then charged into the vessel. All of the iron oxide is then charged into the vessel at room temperature of about 77° F. The temperature of the components in the vessel are heated to a temperature of about 194° F. and agitated for about 2 hours. Agitation is stopped and the temperature maintained at about 194° F. for about another 2 hours. The temperature is then cooled to about 130° F. and about 5.6 grams of the base are charged into the vessel. The components of the vessel are then mixed for about 1 hour. The pH value of the contents in the vessel is about 3.00, and about 4.0 grams of the base are charged into the vessel. The contents of the vessel are heated to a temperature of about 167° F. for about 2 hours, and the contents of the vessel experienced a color change of from reddish to gray. The contents of the vessel are then allowed to cool to about room temperature for a period of about 12 hours. More of the base is charged to the vessel, and the pH value of the contents of the vessel is about 3.72. The contents of the vessel are heated to a temperature of about 167° F., and more of the base is charged to the vessel. The contents of the vessel are maintained at the temperature of about 167° F. for about 1 hour, after which time more of the base is charged into the vessel to bring the pH value of the contents of the vessel to about 3.74. After five additional charges of the base at 10 minute intervals, and maintaining the contents of the vessel in a temperature range of from about 167 to about 185, the contents of the vessel are allowed to cool to room temperature of about 77° F. for a period of about 16 hours. The contents of the vessel are then heated again to a temperature of about 185° F. for about 10 hours, after which time the contents of the vessel are analyzed for iron in solution, pH value, and undissolved iron oxide, as above.

Specific components included in or used to prepare Comparative Example B are set forth in Table 3. All amounts are in parts by weight based on the total weight of the ferric and acid complex, unless otherwise stated.

TABLE 3

| Component | Comparative Ex. B |
|---|---|
| Ferric and Acid Complex | |
| Chelant | 68.92 |
| Base B | 13.71 |
| Iron oxide | 17.37 |
| Total Ferric and Acid Complex in Solvent | 100.00 |
| Total amount of chelant, base, iron oxide, and reaction promoter, pbw based on total weight of components in the vessel | 28.01 |

TABLE 3-continued

| Component | Comparative Ex. B |
|---|---|
| Solvent, pbw based on the total weight of components in the vessel | 71.99 |
| Total | 100.00 |
| Heating time, hours above 180° F. | 14 |
| Heating temperature range, ° F. | 167–194 |
| pH value of final ferric and acid complex in the solvent | 3.8 |
| Iron in solution, pbw based on the total weight of all iron charged into the vessel | 6.3 |
| Undissolved iron oxide, pbw based on the total weight of all iron oxide charged into the vessel | 93.7 |

Chelant is 1,3-propylenediaminetetraacetic acid.
Base A is ammonium hydroxide
Base B is ammonia.
Iron oxide is magnetite.
Reaction promoter A is ferric sulfate.
Reaction promoter B is ferric citrate hydrate.
Reaction promoter C is ferrous sulfate.
Solvent is deionized water.

With reference to Tables 1, 2, and 3, the ferric and acid complexes prepared in accordance with the subject invention require a shorter amount of heating time to obtain greater amounts of iron in solution, as compared to the ferric and acid complexes of the Comparative Examples. As a result, the ferric and acid complex of the subject invention has less undissolved iron oxides, as compared to the Comparative Examples.

The invention has been described in an illustrative manner, and it is to be understood that the terminology which has been used is intended to be in the nature of words of description rather than of limitation. Obviously, many modifications and variations of the present invention are possible in light of the above teachings, and the invention may be practiced otherwise than as specifically described.

What is claimed is:

1. A ferric and acid complex comprising the reaction product of:
   a chelant having at least one carboxylic acid functionality;
   an iron oxide;
   a base; and
   a reaction promoter having an $Fe^{3+}$ ion.

2. A ferric and acid complex as set forth in claim 1 wherein said reaction promoter comprises a ferric salt.

3. A ferric and acid complex as set forth in claim 2 wherein said ferric salt is selected from the group of ferric sulfate, ferric carbonate, ferric chloride, ferric nitrate, ferric bromide, ferric citrate, ferric glycolate, hydrates of said ferric salts, and combinations thereof.

4. A ferric and acid complex as set forth in claim 2 wherein said ferric salt is selected from the group of ferric sulfates, hydrates of said ferric sulfate, and combinations thereof.

5. A ferric and acid complex as set forth in claim 1 wherein said reaction promoter is present in an amount of from 0.03 to 3.5 parts by weight based on the total weight of said ferric and acid complex.

6. A ferric and acid complex as set forth in claim 5 wherein said reaction promoter is present in an amount of about 0.2 parts by weight based on the total weight of said ferric and acid complex.

7. A ferric and acid complex as set forth in claim 1 wherein said chelant comprises an aminopolycarboxylic acid having at least two carboxylic acid functionalities.

8. A ferric and acid complex as set forth in claim 7 wherein said aminopolycarboxylic acid is selected from the group of ethylenediaminetetraacetic acid, nitrilotriacetic acid, iminodiacetic acid, 1,2-propylenediaminetetraacetic acid, N-methyl, ethyl, propyl and butyl iminodiacetic acid, 1,3-propylenediaminetetraacetic acid, N-hydroxyethylethylenediaminetriacetic acid, triethylenetetraminehexaacetic acid, diethylenetriaminepentaacetic acid, and combinations thereof.

9. A ferric and acid complex as set forth in claim 7 wherein said aminopolycarboxylic acid comprises 1,3-propylenediaminetetraacetic acid.

10. A ferric and acid complex as set forth in claim 1 wherein said base is selected from the group of ammonia, ammonium hydroxide, alkyl amines, ethanol amines, propanol amines, alkali hydroxides, earthalkali hydroxides, and combinations thereof.

11. A ferric and acid complex as set forth in claim 1 wherein said iron oxide is selected from the group of magnetite, goethite, lepidocrocite, ferrihydrite, and combinations thereof.

12. A ferric and acid complex as set forth in claim 1 wherein said iron oxide comprises magnetite.

13. A ferric and acid complex as set forth in claim 1 wherein said iron oxide is present in an amount of at least 16 parts by weight based on the total weight of the ferric and acid complex.

14. A process for preparing a ferric and acid complex comprising the steps of:
   charging solvent into a vessel;
   charging a chelant into the vessel;
   charging a base into the vessel;
   charging an iron oxide into the vessel;
   charging a reaction promoter having an $Fe^{3+}$ ion into the vessel; and
   heating the solvent, chelant, base, iron oxide, and reaction promoter in the vessel to a temperature of at least 170° F. for a period of at least about 3 hours to form the ferric and acid complex.

15. A process as set forth in claim 14 further comprising the step of mixing the chelant and the solvent in the vessel for a period of at least 10 minutes prior to charging the base, iron oxide, and reaction promoter into the vessel.

16. A process as set forth in claim 15 wherein the step of charging the base into the vessel comprises charging the base prior to charging the iron oxide and the reaction promoter until a pH value within the vessel is less than about 4.5.

17. A process as set forth in claim 16 wherein the reaction promoter comprises a ferric salt.

18. A process as set forth in claim 14 wherein the reaction promoter is charged in an amount of from 0.03 to 3.5 parts by weight based on the total weight of the ferric and acid complex.

19. A process as set forth in claim 18 wherein the reaction promoter is charged in an amount of about 0.2 parts by weight based on the total weight of the ferric and acid complex.

20. A process as set forth in claim 14 wherein the chelant comprises an aminopolycarboxylic acid having at least two carboxylic acid functionalities.

21. A process as set forth in claim 14 wherein the solvent is water.

22. A process as set forth in claim 14 wherein the step of heating occurs within a temperature range of from about 180° F. to about 212° F.

23. A process as set forth in claim 14 wherein the step of heating occurs for a period of from 3 to 12 hours.

24. A process as set forth in claim 14 further comprising the step of charging additional base into the vessel subsequent to charging the iron oxide and the reaction promoter until a pH value within the vessel is from about 3.6 to about 4.

25. A process as set forth in claim 14 further comprising the step of spray drying the ferric and acid complex.

* * * * *